(12) United States Patent
Garcia Tello et al.

(10) Patent No.: US 9,829,485 B2
(45) Date of Patent: Nov. 28, 2017

(54) BIOSENSOR DEVICE AND METHOD OF MANUFACTURING THE SAME

(75) Inventors: Pablo Garcia Tello, Leuven (BE); Freddy Roozeboom, Waalre (NL)

(73) Assignee: NXP B.V., Eindhoven (NL)

( * ) Notice: Subject to any disclaimer, the term of this patent is extended or adjusted under 35 U.S.C. 154(b) by 532 days.

(21) Appl. No.: 12/743,026

(22) PCT Filed: Nov. 12, 2008

(86) PCT No.: PCT/IB2008/054732
§ 371 (c)(1),
(2), (4) Date: May 14, 2010

(87) PCT Pub. No.: WO2009/063408
PCT Pub. Date: May 22, 2009

(65) Prior Publication Data
US 2011/0118128 A1    May 19, 2011

(30) Foreign Application Priority Data

Nov. 16, 2007 (EP) .................................. 07120853

(51) Int. Cl.
| | | |
|---|---|---|
| *G01N 33/543* | (2006.01) | |
| *G01N 21/17* | (2006.01) | |
| *G01N 21/41* | (2006.01) | |
| *G01N 21/59* | (2006.01) | |
| *G01N 21/62* | (2006.01) | |
| *C40B 60/12* | (2006.01) | |

(52) U.S. Cl.
CPC ....... *G01N 33/54373* (2013.01); *G01N 21/17* (2013.01); *G01N 21/41* (2013.01); *G01N 21/59* (2013.01); *G01N 21/62* (2013.01); *C40B 60/12* (2013.01); *G01N 33/54326* (2013.01)

(58) Field of Classification Search
CPC .. G01N 33/54373; G01N 21/62; G01N 21/59; G01N 21/41; G01N 21/17; C40B 60/12
See application file for complete search history.

(56) References Cited

U.S. PATENT DOCUMENTS

| | | |
|---|---|---|
| 5,501,893 A | 3/1996 | Laermer et al. |
| 6,849,397 B2 | 2/2005 | Nelson et al. |
| 7,922,976 B2 * | 4/2011 | Dutta et al. ................ 422/82.11 |
| 2002/0068018 A1 | 6/2002 | Pepper et al. |
| 2002/0191884 A1 * | 12/2002 | Letant et al. ................... 385/12 |
| 2006/0060766 A1 | 3/2006 | Turner et al. |
| 2006/0234229 A1 * | 10/2006 | Van Beuningen et al. ....... 435/6 |

(Continued)

OTHER PUBLICATIONS

Lehmann et al., J. Electrochem. Soc., 1990, vol. 137, No. 2, pp. 653-659.*

(Continued)

*Primary Examiner* — Jeremy C Flinders

(57) ABSTRACT

A biosensor device for detecting biological particles, the biosensor device comprising a substrate, a regular pattern of pores formed in the substrate, and a plurality of sensor active structures each of which being arranged on a surface of a corresponding one of the pores, wherein each of the plurality of sensor active structures is sensitive to specific biological particles and is adapted to modify electromagnetic radiation interaction properties in the event of the presence of the respective biological particles.

20 Claims, 3 Drawing Sheets

(56) References Cited

U.S. PATENT DOCUMENTS

2006/0276047 A1* 12/2006 Ouyang et al. .............. 438/753
2009/0244532 A1* 10/2009 Letant et al. ................ 356/244
2010/0279886 A1* 11/2010 Fauchet ........... G01N 33/54373
  506/9

OTHER PUBLICATIONS

Ouyang, Huimin, et al; "Label-Free Quantitative Detection of Protein Using Macroporous Silicon Photonic Badgap Biosensors"; Anal. Chem 79; pp. 1502-1506 (2007).

Lee, M., et al; "A Two Dimensional Silicon-Based Photonic Crystal Microcavity Biosensor"; Proceedings of SPIE—The Intl Society for Optic Response of Photonic Bandgap Structures III; vol. 632 (2006).

Badel, X., et al; Formation of Ordered Pore Arrays at the Nanoscale by Electrochemical Etching of N-Type Silicon; Superlattices and Microstructures; Academic Press; London, GB; vol. 36, No. 1-3; pp. 245-253 (Jul. 1, 2004).

Ouyang, Huimin, et al; "Macroporous Silicon Microcavities for Macromolecule Detection"; Advanced Functional Materials; p. 1851-1859; (2005).

Roozeboom, F., et al; "High-Density, Low-Loss MOS Capacitors for Integrated RF Decoupling"; Proceedings $34^{th}$ Intl Symposium on Micoelectronics; Baltimore, MD, US; pp. 477-483 (Oct. 2001).

Van Den Meerakker, J.E.A.M., et al; "Etching of Deep Macropores in 6-In Siwafers"; Journal of the Electrochemical Socciety 147; pp. 2757-2761 (2000).

Lehmann, V., et al; "The Limits of Macropore Array Fabrication"; Thin Solid Films 297; 5 pages (1997).

Van Den Meerakker, J.E.A.M., et al; "Kinetic and Diffusional Aspects of the Dissolution of Si in HF Solutions"; Journal of the Electrochemical Society 148; pp. G166-G171 (2001).

7. MPI-P—CPI Joint Seminar; 19 pages; (Apr. 18-19, 2007).

International Search Report Written Opinion for Application PCT/IB2008/054732 Published May 22, 2009.

Wu et al., "Self-aligned tantalum oxide nanodot arrays through anodic alumina template," www.sciencedirect.com, Microelectronic Engineering 83, Feb. 14, 2006, pp. 1567-1570.

* cited by examiner

BIOSENSOR DEVICE AND METHOD OF MANUFACTURING THE SAME

FIELD OF THE INVENTION

The invention relates to a biosensor device.

Moreover, the invention relates to a method of manufacturing a biosensor device.

Furthermore, the invention relates to a method of use.

BACKGROUND OF THE INVENTION

A biosensor may be denoted as a device that may be used for detecting an analyte that combines a biological component with a physicochemical or physical detector component.

For instance, a biosensor may be based on the phenomenon that capture molecules immobilized on a surface of a biosensor may selectively hybridize with target molecules in a fluidic sample, for instance when an antibody-binding fragment of an antibody or the sequence of a DNA single strand as a capture molecule fits to a corresponding sequence or structure of a target molecule. When such hybridization or sensor events occur at the sensor surface, this may change the electrical or optical properties of the surface, which may be detected as the sensor event.

Huimin Ouyang, Lisa A. DeLouise, Benjamin L. Miller, and Philippe M. Fauchet, "Label-Free quantitative detection of protein using macroporous silicon photonic bandgap biosensors", Anal. Chem 79, 1502-1506 (2007) discloses a label-free biosensor using macroporous silicon (pore size >100 nm) one-dimensional photonic band gap structures that are sensitive to refractive index changes. The disclosure demonstrates that a macroporous silicon microcavity sensor may be used to selectively and quantitatively detect a specific target protein with minimal sample preparation.

However, such a conventional biosensor may lack sufficient accuracy and reproducibility.

OBJECT AND SUMMARY OF THE INVENTION

It is an object of the invention to provide a biosensor having a sufficient resolution.

In order to achieve the object defined above, a biosensor device and a method of manufacturing a biosensor device according to the independent claims are provided.

According to an exemplary embodiment of the invention, a biosensor device for detecting biological particles is provided, the biosensor device comprising a substrate, a regular (i.e. ordered) pattern of pores formed in the substrate, and a plurality of sensor active structures each of which being arranged on a surface of a corresponding one of the pores, wherein each of the plurality of sensor active structures is sensitive to specific biological particles and is adapted to modify electromagnetic radiation interaction properties (such as a refraction index of the biosensor device or of a part thereof) in the event of the presence of the respective biological particles.

According to another exemplary embodiment of the invention, a method of manufacturing a biosensor device for detecting biological particles is provided, the method comprising forming a regular pattern of pores in a substrate, and forming a plurality of sensor active structures each of which are arranged on a surface of a corresponding one of the pores, wherein each of the plurality of sensor active structures is sensitive to specific biological particles and is adapted to modify electromagnetic radiation interaction properties in the event of the presence of the respective biological particles.

According to still another exemplary embodiment of the invention, a biosensor device having the above mentioned features is used for food analysis or water analysis. However, alternative applications are possible, for instance a use for medical purposes such as medical diagnosis.

The term "biosensor" may particularly denote any device that may be used for the detection of an analyte comprising biological molecules such as DNA, RNA, proteins, enzymes, cells, bacteria, virus, etc. A biosensor may combine a biological component (for instance capture molecules at a sensor active surface capable of detecting molecules) with a physical detector component (for instance an optical scanner for sampling optical properties of the biosensor device which are modifiable by a sensor event).

The term "biological particles" may particularly denote any particles which play a significant role in biology or in biological or biochemical procedures, such as genes, DNA, RNA, proteins, enzymes, cells, bacteria, virus, etc.

The term "sensor active region" may particularly denote an exposed region of a sensor, for instance a functionalization of a surface of trenches etched in the substrate and forming a porous structure, which may be brought in interaction with a fluidic sample so that a detection event may occur in the sensor active region. In other words, the sensor active region may be the actual sensitive area of a sensor device, in which area processes take place that form the basis of the sensing.

The term "fluidic sample" may particularly denote any subset of the phases of matter. Such fluids may include liquids, gases, plasmas and, to some extent, solids, as well as mixtures thereof. Examples for fluidic samples are DNA containing fluids, blood, interstitial fluid in subcutaneous tissue, muscle or brain tissue, urine or other body fluids. For instance, the fluidic sample may be a biological substance. Such a substance may comprise proteins, polypeptides, nucleic acids, DNA strands, etc.

The term "electromagnetic radiation" may particularly denote a beam of photons of any appropriate wavelength. This may include the optical spectrum (for instance the range between 400 nm and 800 nm), but may also include electromagnetic radiation of other wavelengths, like UV, infrared, microwaves, or even X-rays. According to exemplary embodiments of the invention, such electromagnetic radiation may be used for scanning a surface of the biosensor device, which may have different refraction indices in the presence and in the absence of the biological particles to be detected.

The term "pores" may particularly denote any recesses or indentations or trenches formed in a surface of a substrate. Such a pore may extend essentially perpendicular to a main surface of the substrate in which the pores are formed. Such a forming of pores may be performed by etching, ablation, milling, etc. Thus, a pore may simply be a hole in a material.

The term "regular pattern of pores" may particularly denote that the arrangement of the pores on the surface of the substrate follows an ordering rule. Thus, the pores are not only provided in a random or statistical manner on the surface, but may be located at dedicated positioned defined in accordance with a certain algorithm or formula defining the arrangement of these pores. Such a regular pattern may be a pattern in which adjacent pores have the same distance from one another in one or two dimensions. Such a regular pattern may also include a fixedly controlled correlation of sizes, dimensions, shapes of the pores, which may be identical at least over a sub-portion of the substrate or over the entire substrate surface. A regular pattern of pores may also include pores arranged parallel to one another, not only being aligned in any arbitrary direction. A regular pattern of pores may also include pores having the same geometrical shape such as a cylindrical shape, not only being aligned in any arbitrary direction. A regular pattern of pores may also include pores extending with the same depth into a substrate. A regular pattern of pores may also include pores having the same cross-sectional area and/or shape at a main surface of the substrate. The regular pattern of pores may be defined deterministically, not statistically or in a random manner. The regularity of the pore pattern may result from a corresponding manufacture procedure, such as a pore formation based on a mask.

The term "modify electromagnetic radiation interaction properties" may particularly denote that in the presence or absence of biological particles interacting with the sensor active structures, the properties according to which a beam of electromagnetic radiation interacts with the pore comprising substrate can be characteristically modified or modulated, thereby allowing to conclude from a change of the electromagnetic radiation interaction properties to the occurrence of a sensor event. Such electromagnetic radiation interaction properties may be a reflectance, a refractive index, a transmission characteristic, an absorption characteristic, etc. of a radiation beam. Such a change may be effected directly by the accumulation of biological particles interacting with the sensor active structure in a pore due to a specific interaction of complementary capture molecules and biological particles as a result of a hybridization, and the change may result from the fact that biological particles may have optical properties which differ from those of the pure biosensor. However, such a change may also be effected indirectly by an impact of accumulated biological particles on surrounding material, since this may also modulate or influence the refraction index of the surrounding material such as a photonic band gap structure.

According to an exemplary embodiment of the invention, a biosensing system is provided in which inner surfaces of pores formed as vertical trenches in a substrate are covered with a material to which biological molecules are sensitive such that a sampling or scanning of the surface with an electromagnetic radiation detection mechanism allows reading out sensor events after an interaction between a fluidic sample under analysis and the sensor active structures on the surface of the pores. According to an exemplary embodiment of the invention, the regular arrangement of the pores on the surface of the substrate may allow for a reproducible and highly accurate detection result, and allows accurately controlling and determining the arrangement of the pores on the substrate.

In contrast to conventional approaches in which an arrangement of the pores as well as a geometry of the pores is purely random, embodiments of the invention benefit from a regular ordered pattern of pores and/or a regular ordered geometrical arrangement of the pore properties to thereby increase the accuracy, since detection signals, for example electromagnetic detection signals, become absolutely comparable due to the regular arrangement of the pores and/or due to the regular geometry of the pores.

Next, further exemplary embodiments of the biosensor device will be explained. However, these embodiments also apply to the method of manufacturing a biosensor device and to the method of use.

The regular pattern of pores may comprise one of the group consisting of a matrix-like pattern and a hexagonal pattern. For example, the pores may be arranged in a pattern formed by rows and columns so that each of the pores can be considered as an element of a matrix according to which the pores are arranged. Therefore, the pores are arranged at cross-sectional points of straight rows and straight columns, for instance in a manner that four adjacent pores form a rectangle. However, it is also possible that the pores provide a hexagonal pattern, which allows for a very compact arrangement of the pores.

The pores may be micropores or nanopores. The term "micropore" may particularly denote that a pore diameter or a distance between the two pores is in the order of magnitude of a micrometer. The term "nanopores" may particularly denote that the order of magnitude of a diameter of the pores and/or a distance between adjacent pores is in the order of magnitude of nanometers. With such an arrangement, which may be manufactured using mask techniques known from semiconductor technology as such, it is possible to obtain a very high density of the pores, thereby allowing for very compact biosensors and a high spatial resolution.

The pores may have a diameter in a range between essentially 5 nm and essentially 5 µm, particularly in a range between essentially 20 nm and essentially 1 µm. The term "diameter" may denote a diameter of a circular surface of the pores, in case of a cylindrical pore. However, as an alternative to a cylindrical pore, it is also possible that the surface is polygonal, for instance triangular, rectangular, pentagonal, etc. Also an oval pore surface is possible.

The depth of the pores, i.e. deepness or an extension of the trenches formed in the substrate and serving as the pores, may be in a range between essentially 10 nm and essentially 100 µm, particularly in a range between essentially 100 nm and essentially 10 µm. Oblong pores having a high aspect ration (i.e. relationship of depth to diameter) of for instance at least five, particularly of at least ten, more particularly of at fifty, have the advantage that a large sensor active surface can be covered with a functionalization material, i.e. the sensor active structures, in order to allow for an accurate detection of the biological molecules.

The rectangular pattern of pores may be divided into a plurality of sub-groups, wherein different sub-groups of pores may differ regarding at least one property, which is relevant for the biosensing capability. Thus, the entire surface of the biosensor device or of the substrate can be divided into a plurality of portions each of which being foreseen for another sensor purpose. Each of the portions may be sensitive to a specific biological molecule or kind of molecules, and different portions may be sensitive to different biological molecule or kind of molecules. Therefore, pores in one and the same sub-group may have the same biosensing properties, whereas pores of different sub-groups may have differing biosensing properties. Such differing properties may be differing diameter resulting in a sensitivity regarding biological particles (for instance proteins, DNA, viruses, bacteria) of different sizes. By adjusting the diameter of the pores, it may be adjusted which kind of particles may penetrate into the pore due to a correlation between pore size and molecule size. Furthermore, such a biosensing property may be the volume of the pore. Only particles having a volume less or equal than the volume of the pore may be able to enter the pore. The kind of sensor active structures may differ between the different sub-groups. For example, oligonucleotides serving as capture molecules for different kind of DNA may be immobilized in different portions of the surface. Thus, by grouping the pores on the surface of the biosensor device in accordance with different sensor tasks, scanning the surface may allow detection of various or several biological particles simultaneously, which may be included in a mix of a fluidic sample. By having a plurality of pores in each of the sub-groups it is possible to increase the accuracy, since in very diluted samples it may be possible that only a few of the pores of each sub-groups is hybridized with a corresponding particle.

The substrate may comprise a photonic band gap (PBG) structure. PBG structures are highly sensitive to changes in the refractive index of the environment. This makes PBG structures an ideal candidate for ultrasmall and efficient lab-on-a-chip devices.

Each of the plurality of sensor active structures may be adapted to modify, in the event of the presence of the respective biological particles, at least one of the group consisting of electromagnetic radiation reflection properties, electromagnetic radiation transmission properties, electromagnetic radiation absorption properties, and electromagnetic radiation wavelength properties. Thus, it is possible with the biosensor according to exemplary embodiments of the invention to measure the sensor response of the functionalized surface of the biosensor device by impinging electromagnetic radiation such as light on the biosensor. As a response to this radiation, the reflection spectrum, the transmission spectrum, an absorption spectrum, or a wavelength shift due to the sensor event can be detected.

The substrate may comprise one of the group consisting of a semiconductor substrate, particularly a silicon substrate, a germanium substrate or any other group IV semiconductor substrate, or a group III-group V semiconductor substrate such as gallium arsenide. Alternatively, the substrate may be any other substrate such as a glass substrate, a plastics substrate or even an aluminium substrate.

The biosensor device may comprise one or more electromagnetic radiation sources adapted for generating electromagnetic radiation to be directed towards the substrate. Such an electromagnetic radiation source may be a laser, particularly a semiconductor laser such as a laser diode. Such a laser diode may be provided in common for the entire substrate surface or only for a part of the optical fibers, wherein one or more optical elements such as mirrors, lenses, apertures, beam splitters, optical couplers, diffusers, etc. may be used for directing the light towards the pores. Alternatively, a separate laser diode may be provided for individual ones of different substrate surface portions. Also light emitting diodes may be implemented as electromagnetic radiation source.

The biosensor device may further comprise one or more electromagnetic radiation detectors adapted for detecting electromagnetic radiation after interaction with the substrates and the components located thereon and therein. Such an electromagnetic radiation detector may comprise one or more photodiodes, or may comprise a two-dimensional or one-dimensional detector array such as a CCD (charge coupled device).

The biosensor device may comprise one or more capture molecules arranged at a surface of each of the plurality of sensor active structures being adapted for interacting with the biological particles. Thus, the capture molecules may be different for different ones of the sensor active structures so that a massive parallel analysis of a fluidic sample may be performed with the result that at specific pores, where capture molecules having a complementary sequence to fractions of the biological particles are present, sensor events may be detected.

The biosensor may be manufactured in CMOS technology. CMOS technology allows manufacturing structures with very small dimensions so that (spatial) accuracy of the device will be improved by implementing CMOS technology. A BiCMOS process may be used as well, wherein BiCMOS in fact is a CMOS process with some additional processing steps to add bipolar transistors. The same holds for CMOS processes with other embedded options like embedded flask, embedded DRAM, etc. In particular this may be relevant because the presence of an option often provides opportunities to use additional materials that come with the options "at zero cost". For instance, an appropriate high-k material (an insulating material with a high dielectric constant, for example aluminium-oxide) that comes with an embedded DRAM process can be used "at zero cost" for any desired purpose.

The biosensor device may be monolithically integrated in a semiconductor substrate, particularly comprising one of the group consisting of a group IV semiconductor (such as silicon or germanium), and a group III-group V semiconductor (such as gallium arsenide).

Next, further exemplary embodiments of the manufacturing method will be explained. However, these embodiments also apply to the biosensor device and to the method of use.

The regular pattern of pores may be formed in a substrate using a mask, particularly using one of the group consisting of a lithography mask and a hard mask. Such a mask may also be denoted as reticle. A mask may be a plate (for instance a glass plate) with a pattern of transparent and opaque areas used to photolithographically create patterns on the substrate such as a wafer. The pattern on the mask may correspond to or may be mapped to the pattern of the pores to be generated on or in the surface of the substrate. Such a mask may be used in the context of photolithography, i.e. may allow to pattern the surface of the below substrate correspondingly to a pattern of optically transmissive and absorptive surface areas. Such a mask may serve as an etching mask having portions through which an etchant may penetrate and portions through which an etchant may not penetrate. The use of a mask is an important feature, which allows manufacturing the regular pattern of pores.

The regular pattern of pores may be formed by an etching procedure using the mask, particularly by an etching procedure of the group consisting of a wet etching and a dry etching. Wet etching may be chemical etching performed with a liquid etchant, as opposed to a plasma. Dry etching may refer to the removal of material, for instance a masked pattern of semiconductor material, by exposing the material to a bombardment of ions (for instance a plasma of nitrogen, chlorine and boron trichloride) that dislodge portions of the material from the exposed surface.

The method may comprise adjusting the properties (particularly properties relevant for biosensing) of the regular pattern of pores by adjusting at least one parameter during the etching procedure, for instance the etching time, the etchant, an illumination, etc. Therefore, the regular pattern of pores may be tailored to specific requirements of a specific application for instance may be designed regarding shape, size, dimension, etc.

The method may comprise surface functionalizing a surface of the pores. Therefore, the surface of the pores may be specifically treated so as to specifically modify their surface properties of specific portions of the pores. This may include the generation of a pattern of hydrophobic and hydrophilic sections, sensor active sections and non-sensor active sections, different sensor portions having different sensing properties, etc.

According to an exemplary embodiment of the invention, a biosensor device may be provided which is particularly suitable for food or water analysis. Such a biosensor may be a CMOS-compatible label-free biosensor. It may be applied in the field of analytical testing. Specialized laboratories located away from a patient, a doctor, a hospital may perform nearly all of the testing causing significant time delays in reporting results. Embodiments of the invention meet a demand for biomedical sensors with advanced microfabrication and signal processing techniques that are inexpensive, accurate and reliable. With an average detection time in the order of a few minutes it may be possible to significantly reduce the delay time as well as to bring the testing to doctor's offices and patient's homes. An attractive embodiment in this respect allows for a label-free detection of biomolecules of interest.

More particularly, an embodiment of the invention provides a way of manufacturing a biosensor that allows for label-free detection of biomolecules/organisms present in very low concentration and that can be fabricated using CMOS technology.

According to an exemplary embodiment of the invention, a label-free optical biosensor may be provided which may use photonic band gap (PBG) structures for sensing applications. PBG structures may be highly sensitive to changes in the refractive index of the environment, and such changes may occur where an electric field is maximum. This makes PBG structures specifically appropriate for very small and efficient lab-on-chip devices.

Ordered porous silicon PBG structures can be used as an optical label-free sensing platform for chemical and biological detection. Advantages of using a silicon substrate having a regular pore pattern include easy fabrication and compatibility with silicon microelectronics technology. The large internal surface area of such a material can be chemically modified for the capture and selective detection of different types of molecules such as DNA, proteins, gram-negative bacteria, and enzymes. The nanomorphology of the ordered porous silicon layers can be adjusted to be in accordance with specific biosensing applications. The pore size not only determines the size of the molecules that can infiltrate the pores but it also impacts the sensor sensitivity. Although the sensitivity of the biosensor decreases as the pore size increases, large sized pores (>100 nm) are useful for the detection of micromolecules (for instance immunoglobin) that cannot infiltrate into devices with small pores (<30 nm). Ordered PBG structures with pore diameters in the 20 nm to 50 nm range are well suited for the detection of smaller molecules (for instance less than 50 kDa).

Exemplary embodiments of the invention provide a fabrication method that allows the tailoring of PBG structures with desired and precise pore diameters. Moreover, the controlled fabrication of different array structures of pores with different diameters integrated in the same sensing areas may allow to perform measurements of a large variety of analytes in the same run. This may increase enormously the multiplexing capabilities of any biosensing device. Therefore, according to an exemplary embodiment of the invention, an increased control of pore diameter is enabled, and therefore device sensitivity. Further it is possible to increase multiplexing sensing capabilities, and therefore the device performance is improved. Furthermore, device versatility can be improved.

According to an exemplary embodiment of the invention, a porous biosensor is provided having a size or a pitch of nanopores, which may be properly controlled, having an impact on sensor sensitivity. Therefore, in contrast to the creation of a random arrangement of nanopores, the pore size and pitch is properly controlled according to exemplary embodiments of the invention, so that an ordered structure of nanopores may be provided. To obtain such an ordered array of nanopores, a mask may be used to define such a regular pattern. Such a mask may be used, for example, in combination with lithography. More generally, a mask is used in order to define a regular pattern of pores for a biosensor.

It is believed that the pore size not only determines the size of the molecules that can infiltrate the pores but it also impacts the sensor sensitivity. Therefore, a controlled fabrication procedure allows for an optimum control of the pore size and pitch so that the performance of the biosensing device is fully controllable. Otherwise, pores of random sizes and/or random-spaces lead to uncontrolled performance and/or calibration of the biosensing device. Exemplary embodiments of the invention allow controlling precisely such factors as pore size and spacing.

The provided fabrication procedures do control the morphology of the device and allow therefore for a proper performance. Furthermore, such a fabrication process is suitable to be integrated in a standard CMOS technology. It does not require to make use of any non-standard material or technique. Pore size and spacing may be controlled, and controlled pore and sizes of different types may be created, wherein a pore size, for instance, can be tuned up by the choice of substrate wafer, dopant level and/or anodic current.

According to exemplary embodiments of the invention multiplexing capability may be obtained, which enables detecting more than one analyte per sensor and per run of the device hence reducing the cost of the assays, reagents, etc.

The biosensor chip or microfluidic device may be (or may be part of) a sensor device, a sensor readout device, a lab-on-chip, an electrophoresis device, a sample transport device, a sample mix device, a sample washing device, a sample purification device, a sample amplification device, a sample extraction device or a hybridization analysis device. Particularly, the biosensor or microfluidic device may be implemented in any kind of life science apparatus.

For any method step, any conventional procedure as known from semiconductor technology may be implemented. Forming layers or components may include deposition techniques like CVD (chemical vapour deposition), PECVD (plasma enhanced chemical vapour deposition), ALD (atomic layer deposition), or sputtering. Removing layers or components may include isotropic or anisotropic etching techniques like wet etching, plasma etching, etc., as well as patterning techniques like optical lithography, UV lithography, electron beam lithography, etc.

Embodiments of the invention are not bound to specific materials, so that many different materials may be used. For conductive structures, it may be possible to use metallization structures, silicide structures or polysilicon structures. For semiconductor regions or components, crystalline silicon may be used. For insulating portions, silicon oxide or silicon nitride may be used.

The biosensor may be formed on a purely crystalline silicon wafer or on an SOI wafer (Silicon On Insulator).

Any process technologies like CMOS, BIPOLAR, BICMOS may be implemented.

The aspects defined above and further aspects of the invention are apparent from the examples of embodiment to be described hereinafter and are explained with reference to these examples of embodiment.

BRIEF DESCRIPTION OF THE DRAWINGS

The invention will be described in more detail hereinafter with reference to examples of embodiment but to which the invention is not limited.

DESCRIPTION OF EMBODIMENTS

Figure 1:
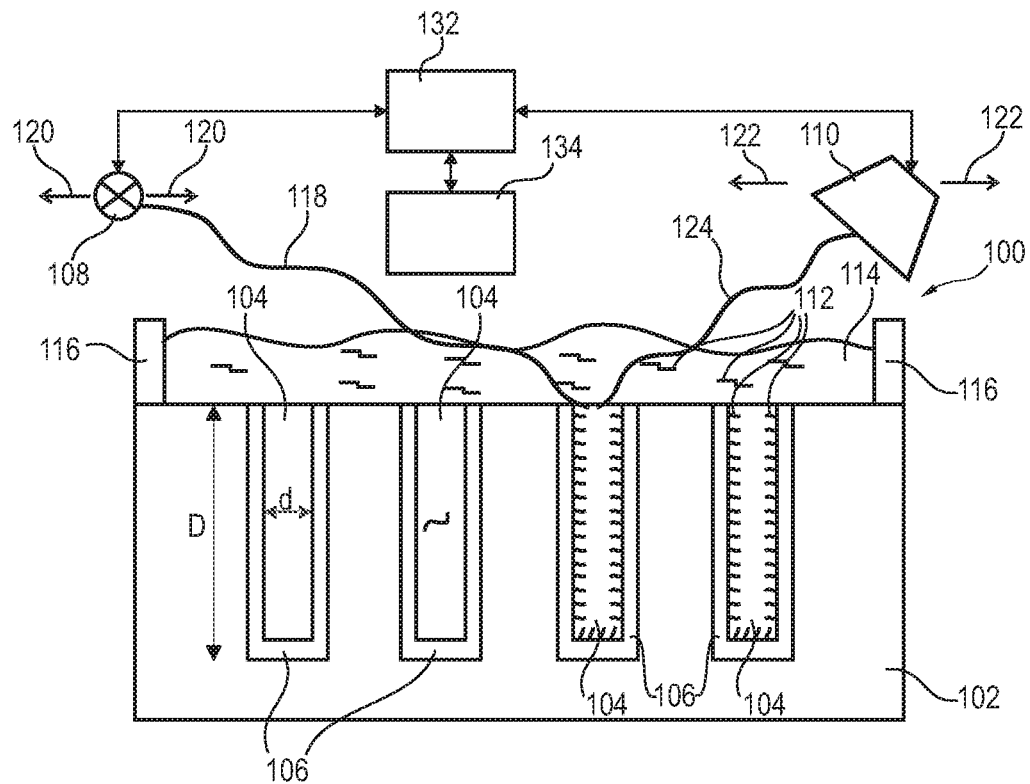
FIG. 1, FIG. 4 to FIG. 6 show biosensor devices according to exemplary embodiments of the invention.

The illustration in the drawing is schematical. In different drawings, similar or identical elements are provided with the same reference signs.

In the following, referring to FIG. 1, a biosensor 100 according to an exemplary embodiment of the invention will be explained.

The biosensor device 100 is adapted for detecting biological particles and comprises a silicon substrate 102 and a regular rectangular two-dimensional pattern of pores 104 (FIG. 1 shows a cross-section so that only a one dimensional arrangement of pores 104 can be seen) formed in the silicon substrate 102. As can be taken from FIG. 1, the pores 104 have a depth, D, of 1 μm and have a diameter, d, of 20 nm, in the present example. The pores 104 are arranged equidistantly from one another, in a direction within the paper plane of FIG. 1 and in a direction perpendicular thereto. Furthermore, sensor active structures 106 are arranged on a surface of trenches forming the pores 104, wherein each of the sensor active structures 106 is sensitive with regard to specific biological particles and is adapted to modify the electromagnetic radiation reflection properties of the corresponding portion of the substrate 102 in the presence of the respective biological particles in a sample 114 under analysis which is brought in contact with the surface of the pore comprising substrate 104 using sample chamber boundary elements 116. For example, using a pipette or an autosampler device, the fluidic sample 114 may be injected on an active surface of the sensor 100.

A laser diode 108 is provided as an electromagnetic radiation source adapted for generating an electromagnetic radiation beam 118 that may be directed onto a surface of the substrate 102. More particularly, the electromagnetic radiation source 108 is movable (which is indicated by arrows 120) for scanning the surface of the substrate 102 to read out a result of a biochemical assay. Thus, by moving the electromagnetic radiation source 108, the surface of the substrate 102 may be scanned. Furthermore, an electromagnetic radiation detector 110 such as a CCD or a photodiode is provided, which may be moved as well (indicated by arrows 122). The electromagnetic radiation detector 110 is adapted for detecting the electromagnetic radiation beam 124 after reflection by a surface portion of the silicon substrate 102. Thus, the orientation of the electromagnetic radiation source 108 and the orientation of the detector 110 with respect to one another is such that the detector 110 may detect secondary electromagnetic radiation 124 in response to the impingement of the primary electromagnetic radiation beam 118 originating from the light source 108.

The sensor active structures 106 in the various pores 104 comprise capture molecules, which are adapted for interacting with the biological particles under investigation. In the present embodiment, biological particles 112 of the sample 114 have a base sequence, which is complementary to a base sequence of the capture molecules in the two pores 104 provided on the right-hand side of FIG. 1. In contrast to this, the sequence of the capture molecules of the two pores 104 on the left-hand side of FIG. 1 are not complementary with biological particles of the fluidic sample 114, and therefore do not show a hybridization reaction. Thus, the interaction between the biological molecules 112 and the sensor active structures 106 is highly selective.

When the electromagnetic radiation source 108 and the electromagnetic radiation detector 110 scan the surface of the substrate 102, no modification of the measured signals with and without sample 114 can be measured when the light beam 118 impinges on the two pores 104 on the left-hand side of FIG. 1. In contrast to this, a change in the refraction index may be detected (and thus a change of the measured signals with and without sample 114) when a hybridization event occurs between the sensor active surface 106 of the two pores 104 on the right-hand side of FIG. 1 on the one hand and the biological particles 112 on the other hand. Therefore, when the electromagnetic radiation beam 118 impinges on the two pores 104 on the right-hand side of FIG. 1, the detector 110 will detect a modification of the electromagnetic radiation interaction properties of the substrate 102, particularly will detect a change in the reflectivity of the substrate 102.

The biosensor device 100 further comprises an evaluation unit 132 which may also be denoted as a control unit and which may be a microprocessor or a central processing unit (CPU). The evaluation unit 132 is adapted for evaluating the detection to thereby identify the biological particles 112. The evaluation unit 132 is unidirectionally or bidirectionally coupled with the light source 108, is unidirectionally or bidirectionally coupled with the detector 110, and is unidirectionally or bidirectionally coupled with an input/output unit 134. Via the input/output unit 134, a user is able to communicate with the evaluation unit 132. The input/output unit 134 may comprise an input element such as a keypad, buttons, or a joystick and may comprise an output element such as a display device. Via the input element of the input/output unit 134, a user may provide the evaluation unit 132 with control commands, whereas results of the detection may be displayed on the output unit of the input/output device 134.

The biosensor device 100 may be manufactured in CMOS technology and may be formed with manufacturing procedures of silicon technology.

In the following, referring to FIG. 2, a method of manufacturing a biosensor device according to an exemplary embodiment of the invention will be explained.

The embodiment of FIG. 2 allows to manufacture a pore array with various pore diameters, as will be explained in the following.

Figure 2:
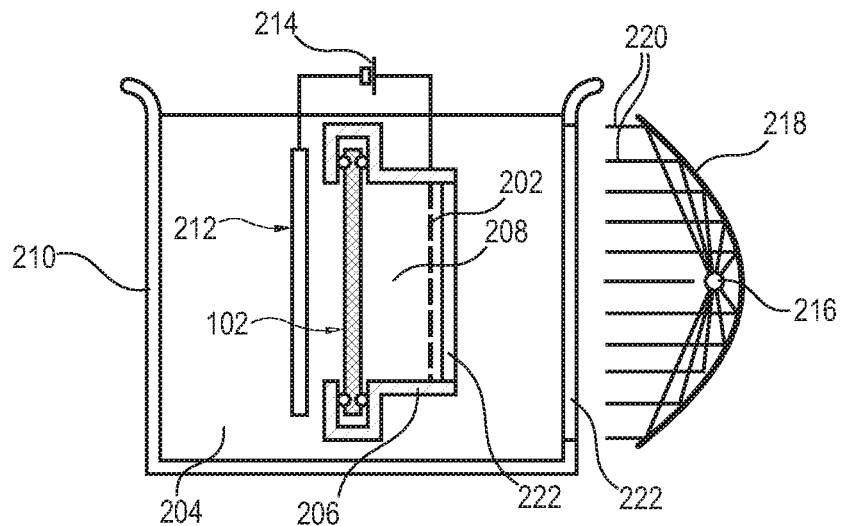
FIG. 2 shows an arrangement for manufacturing a biosensor device according to an exemplary embodiment of the invention.

The embodiment of FIG. 2 is based on a wet etching procedure of pore arrays. Photolithography can be used to apply a silicon nitride ($Si_3N_4$) mask (not shown) with, for example, a closely packed hexagonal array of circular openings with 300 nm to 10 μm diameter and similar spacing onto lightly n-typed (for instance phosphorous) doped (10 Ωcm) 6 inch (100) silicon wafers 102. First, an array of {111} oriented micro-indentations is pre-etched using etching with hot KOH.

The experimental setup for the (photo)electrochemical etching in diluted HF solution 204 is shown in FIG. 2. The wafer 102 is placed in a polypropylene holder 206 containing a $K_2SO_4$ electrolyte 208, used for a uniform anodic contact at the wafer backside. The contact is made through a platinum grid anode 202 placed in the electrolyte 208. The holder 206 is placed in the aqueous HF solution 204 filled in a container 210. The wafer 102 front side is facing the Pt cathode 212. Between the cathode 212 and an anode 202, a current source 214 is connected.

A tungsten halogen lamp 216 is arranged cooperating with a reflector 218 to generate a parallel beam of light 220 which illuminates the wafer 102 backside through transparent polycarbonate windows 222 in the wafer holder 206 and in the etch bath container 210.

The pore diameter may be controlled by the anode current which on its turn is controlled by the light intensity. The current may be monitored and used to adjust the lamp power in an automated cycle. Typical etch conditions for an array of pores with 1.5 µm diameter and 3.5 µm spacing are 7.5 V bias and 0.7 A, using a 1.45 M HF/4.62 M ethanol solution which is circulated through a thermostat by a pneumatic Teflon pump. The etch rate at 30° C. may be typically 0.6 µm/min, but may also be 4 µm/min.

Figure 3:
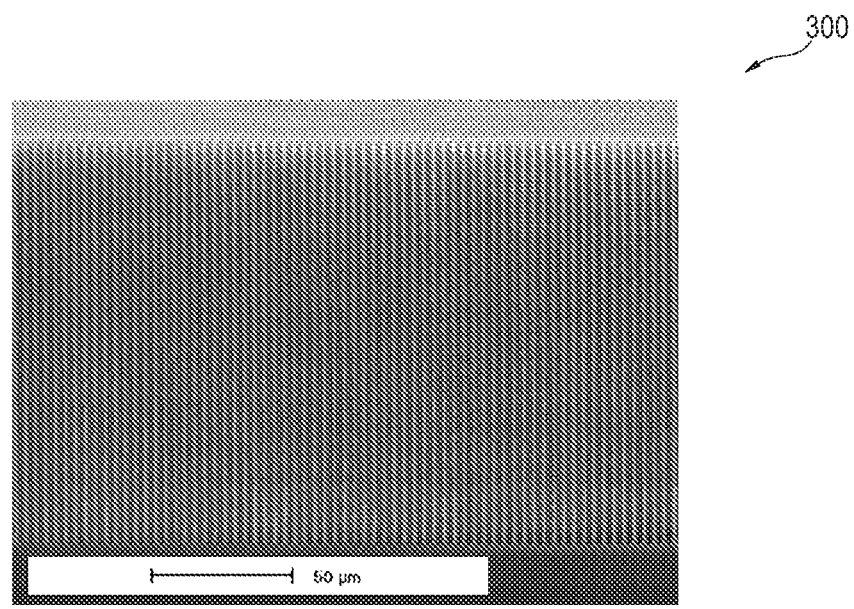
FIG. 3 shows an SEM image illustrating an ordered pore structure of a biosensor device according to an exemplary embodiment of the invention.

FIG. 3 shows an SEM image 300 of a wet etched pore array according to the above-described procedure, wherein the image 300 clearly shows that a regular pattern of pores can be obtained. FIG. 3 shows the excellent depth and diameter uniformity obtained with this etch technique.

The optimum pore size for a specific application may be influenced by the choice of substrate wafer dopant level, which may be limited. In one embodiment, the optimum dopant level may range from 0.1 Ωcm for 0.2 µm wide pores to 40 Ωcm for a maximum 10 µm wide pores.

As one alternative to the procedure illustrated referring to FIG. 2, a dry etching of pore arrays is possible. Such a dry etching process may be performed by reactive ion etching (RIE). Here, an advantage is that one is completely independent of the type and level of substrate doping. Thus, one can directly use highly doped silicon substrate wafers.

An appropriate RIE process is the so-called "Bosch" process, where in a time multiplexed way the pores are etched anisotropically by alternatingly introducing $SF_6/O_2$ and $C_4F_8$ gas into the plasma. The former gas etches the pore and the latter forms a Teflon-like passivation layer on the pore walls.

A hard mask with openings of practically any size, shape and spacing can be used to make a whole pattern in a mask stack of typically 1 µm to 2 µm thermal oxide on top. Next, the wafers are etched in an inductively coupled plasma (ICP) reactor. Typical etching conditions are 12 to 16 mTorr pressure and 20° C. temperature, yielding etch rates varying from 0.5 µm/min for sub-micron diameter pores to 10 µm/min or more for pores with about 10 µm diameter. With this process, a smooth pore wall with a rounded bottom characterizes the macropore structures.

Next, surface modification of the pores according to exemplary embodiments will be explained.

After hard oxide mask removal, for instance by using BOE (buffered oxide etch), a next step can be a surface modification of the internal surface structure to facilitate or accomplish a certain functionalization of the pore walls with respect to the biosensing. Thus, the wetting properties or contact angle of the inner surface of the pores can be adjusted/tuned by using different coatings on the silicon, making up for different surface modification (hydrophobic versus hydrophilic nature). One example is a hydrophilic coating as phosphorsilicate (PSG). Another example might be the deposition of parylene by low pressure CVD (chemical vapor deposition), which may be done at room temperature, or other polymers. Other deposition techniques may also be used, such as dip coating, spray coating, etc.

Additionally, the contact angle of the pores can be modified and made hydrophobic by evaporating or dip coating with silane-based compounds, for instance octadecyl-trichlorosilane or fluorinated compounds such as trimethoxy (3,3,3-trifluoropropyle) silane.

In the following, referring to FIG. 4 and FIG. 5, an exemplary use of exemplary embodiments of the invention will be explained.

Figure 4:
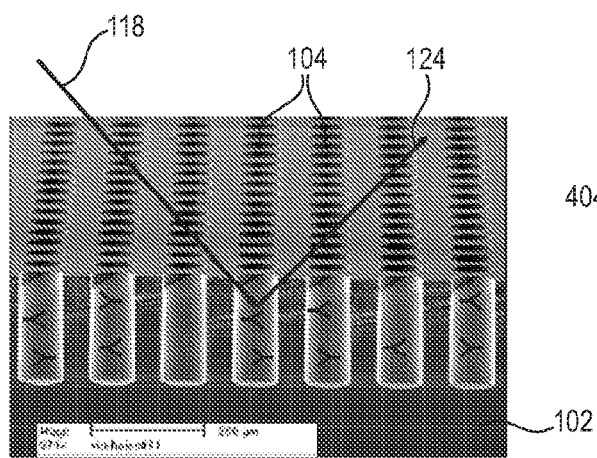
Figure 4:
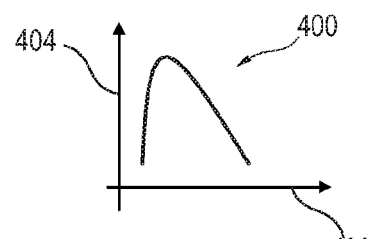

FIG. 4 illustrates a schematic view of a regular two-dimensional arrangement of pores 104 formed in a silicon substrate 102. An impinging light beam 118 is reflected on a surface portion and then forms a beam 124. When detecting the beam 124, a characteristic as shown in the diagram 400 can be obtained, having an abscissa 402 along which a wavelength is plotted and having an ordinate 404 along which a reflectance is plotted. However, as can be seen in FIG. 5, after interaction of particles to be detected 112 with the surface of the pores 104, a shift in the reflectance characteristic can be measured, as seen in the diagram 500 and as indicated by an arrow 502.

Thus, it is possible to measure the reflectance depending on the wavelength. Alternatively, it is also possible to measure a transmission, for instance when a thin substrate is used or a transparent substrate is used.

Figure 5:
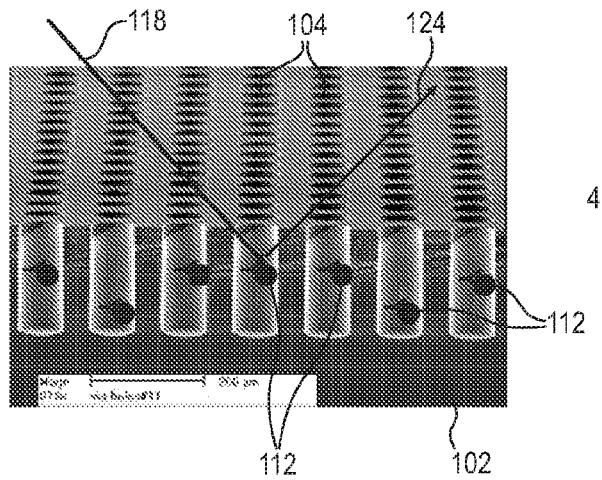
Figure 5:
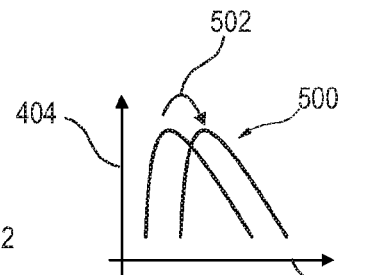
Figure 6:
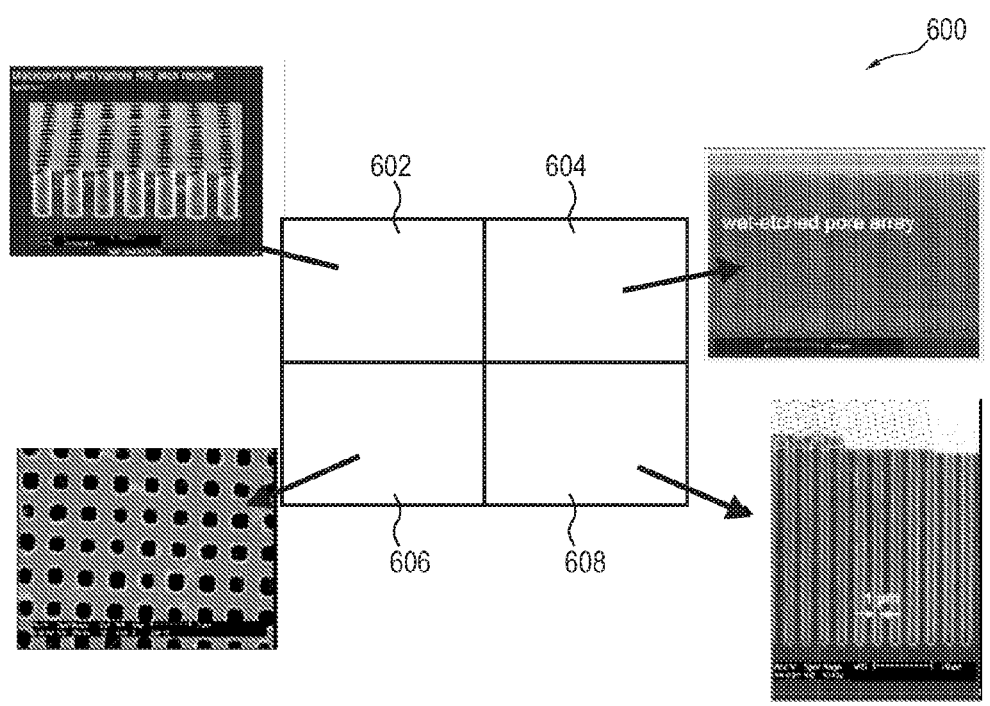

In the embodiment shown in FIG. 4 and FIG. 5, an arrangement of pores 104 having a circular cross-section is shown. The substrate 102 is made of silicon, but may alternatively be made of different materials. A distance between two centers of gravities of adjacent pores 104 may be denoted as the pitch.

Figure 7:
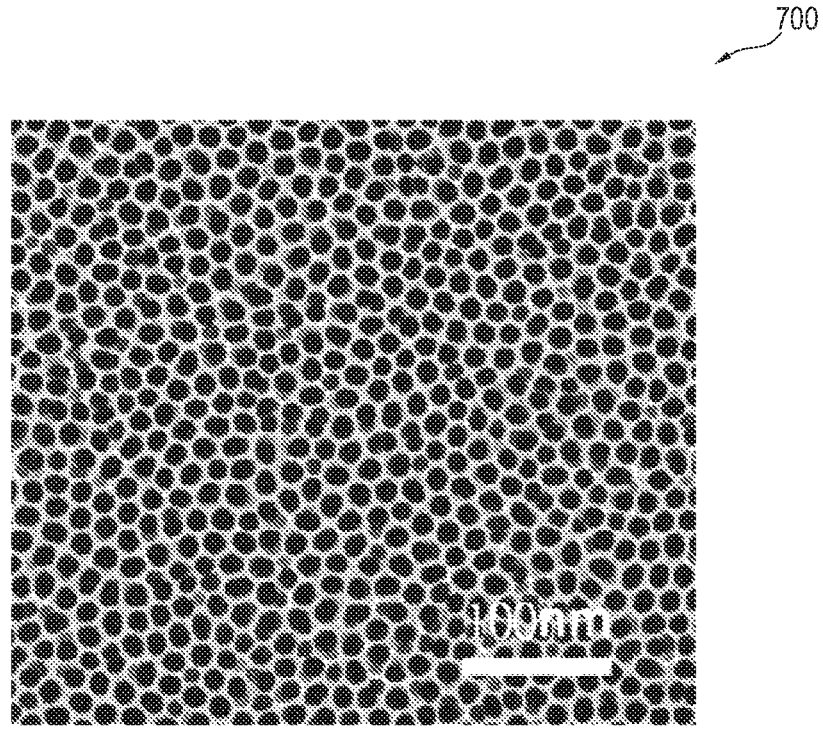
FIG. 7 shows an image illustrating a conventional random pore array.

In contrast to embodiments of the invention, conventional approaches such the one as shown in FIG. 7 do not allow to obtain ordered structures of nanopores, but merely random structures, as can be taken from the image 700. This shows nanopores in aluminium according to a conventional technique in which no regular pattern of pores can be obtained.

Finally, it should be noted that the above-mentioned embodiments illustrate rather than limit the invention, and that those skilled in the art will be capable of designing many alternative embodiments without departing from the scope of the invention as defined by the appended claims. In the claims, any reference signs placed in parentheses shall not be construed as limiting the claims. The words "comprising" and "comprises", and the like, do not exclude the presence of elements or steps other than those listed in any claim or the specification as a whole. The singular reference of an element does not exclude the plural reference of such elements and vice-versa. In a device claim enumerating several means, several of these means may be embodied by one and the same item of software or hardware. The mere fact that certain measures are recited in mutually different dependent claims does not indicate that a combination of these measures cannot be used to advantage.

The invention claimed is:

1. A biosensor device for detecting biological particles, the biosensor device comprising
    a substrate;
    a regular pattern of pores formed in, and defined by, recesses formed in a surface of the substrate and including sub-groups of pores having different sized-based biosensing characteristics, relative to other sub-groups of pores, each of the pores having sidewalls defining an opening at a common surface of the substrate and extending into the substrate, wherein the regular pattern follows an ordering rule; and
    a plurality of sensor active structures each of which include a material and are-arranged on a surface of a corresponding one of the pores, wherein each of the plurality of sensor active structures on the substrate is sensitive to specific biological particles and is adapted to modify electromagnetic radiation reflection properties of the biosensor device in an event of a presence of the respective biological particles, wherein the regular pattern of pores comprises one of the group consisting of a matrix-like pattern, a pattern in which the pores are arranged in rows and columns perpendicular to the rows, and a hexagonal pattern, the regular pattern includes at least one hydrophobic section of pores and at least one hydrophilic section of pores, wherein the at least one hydrophobic and hydrophilic section of pores includes pores with a hydrophobic or hydrophilic coating on an inner surface of the pores and the regular pattern which follows an ordering rule includes at least one of:
  a pattern in which adjacent pores have the same distance from one another in one or two dimensions,
  pores having a fixedly controlled correlation of sizes, dimensions, and shapes,
  pores arranged parallel to one another,
  pores having the same geometrical shape,
  pores extending with the same depth into a substrate,
  pores having the same cross-sectional area or shape at a main surface of the substrate, and
  deterministically-defined pores.

2. The biosensor device of claim 1, wherein the pores are micropores or nanopores defined by the recesses formed in the surface of substrate, and wherein
  a first one of the sub-groups of pores includes a first type of the sensor active structures that is responsive to a first type of the biological particles by modifying the electromagnetic radiation reflection properties in a first manner, and
  a second one of the sub-groups of pores includes a second type of the sensor active structures that is responsive to a second type of the biological particles that is different than the first type of the biological particles, by modifying the electromagnetic radiation reflection properties in a second manner that is different than and detectable relative to the first manner.

3. The biosensor device of claim 1, wherein the pores defined by the recesses formed in the surface of substrate have a diameter at a surface of the substrate in a range of about 5 nm to about 5 μm.

4. The biosensor device of claim 1, wherein the pores defined by the recesses formed in the surface of substrate extend into a surface of the substrate to a depth in a range of about 10 nm to about 100 μm.

5. The biosensor device of claim 1, wherein the sub-groups of pores differ regarding at least one biosensing property, wherein the electromagnetic radiation reflection properties include electromagnetic radiation beams after reflection by the sensor active structures of the substrate.

6. The biosensor device of claim 5, wherein the at least one biosensing property comprises at least one of the group consisting of a diameter of the pores, a depth of the pores, a volume of the pores, and probes of the sensor active structures arranged in the pores.

7. The biosensor device of claim 1, wherein the substrate comprises a photonic band gap structure, and wherein the pores are arranged in a pattern in which the center of each pore is at a regularly-spaced location in a pattern of the pores, relative to the center of the other pores, and wherein the biosensor device is further configured and arranged to detect the presence of the respective biological particles using label-free detection.

8. The biosensor device of claim 1, wherein each of the plurality of sensor active structures is adapted to further modify, in the event of the presence of the respective biological particles, at least one of the group consisting of, electromagnetic radiation transmission properties, electromagnetic radiation absorption properties, and electromagnetic radiation wavelength properties.

9. The biosensor device of claim 1, wherein the substrate comprises one of the group consisting of a semiconductor substrate, a silicon substrate, a germanium substrate, a group IV semiconductor substrate, a group III-group V semiconductor substrate, a glass substrate, and a plastics substrate.

10. The biosensor device of claim 1, comprising an electromagnetic radiation source adapted for generating electromagnetic radiation to be directed towards the regular pattern of pores.

11. The biosensor device of claim 1, comprising an electromagnetic radiation detector adapted for detecting electromagnetic radiation after interaction with the regular pattern of pores.

12. The biosensor device of claim 1, comprising one or more capture molecules arranged at a surface of each of the plurality of sensor active structures and being adapted for interacting with the biological particles.

13. The biosensor device according to claim 1, comprising an evaluation unit, including a processing circuit, and adapted for evaluating the detection to thereby identify the biological particles.

14. The biosensor device according to claim 1, manufactured in CMOS technology and including a label-free biosensor device configured and arranged to detect the presence of the respective biological particles using label-free detection.

15. The biosensor device of claim 1, wherein pores defined by the recesses formed in the surface of the substrate in at least one of the sub-groups of pores have a different pore diameter than a pore diameter of pores in another one of the sub-groups of pores.

16. The biosensor device of claim 1, wherein pores defined by the recesses formed in the surface of substrate in at least one of the sub-groups of pores have a different pore volume than a pore volume of pores in another one of the sub-groups of pores.

17. An apparatus comprising:
  a substrate configured and arranged with sets of recessed pores, and defined by, recesses or indentations formed in a surface of the substrate, at least one of the sets of recessed pores having differing sized-based biosensing properties than another set of recessed pores, each of the pores having an opening at a common surface of the substrate;
  an electromagnetic radiation source configured and arranged to generate electromagnetic radiation directed towards the sets of recessed pores;
  a plurality of sensor active structures, each of which include a material and are on sidewalls of the sets of recessed pores, the plurality of sensor active structures configured and arranged to exhibit electromagnetic radiation reflection properties that are responsive to respective biological particles; and
  an electromagnetic radiation detector configured and arranged to detect different ones of the respective biological particles based on differently-modified electromagnetic radiation reflection properties of the sensor active structures, wherein the electromagnetic radiation reflection properties include electromagnetic radiation beams after reflection by the sensor active structures of the substrate.

18. The apparatus of claim 17, wherein the differing sized-based biosensing properties include pore diameter and pore volume, and the substrate includes at least one of a hydrophobic section of the pores and at least one of a hydrophilic section of the pores, wherein the at least one hydrophobic and hydrophilic section of pores includes pores with a hydrophobic or hydrophilic coating on an inner surface of the pores.

19. The apparatus of claim 17, wherein the sets of recessed pores defined by the recesses or indentations formed in the surface of substrate include pores having openings that are adjacent one another at the common surface and that have different sized-based biosensing properties includes different pitches, and wherein the electromagnetic radiation detector is configured and arranged to detect a first type of the biological particles in response to detecting a first electromagnetic radiation reflection characteristic, and to detect a second type of the biological particles in response to detecting a second electromagnetic radiation reflection characteristic.

20. The device of claim 1, wherein first and second ones of the pores have openings adjacent one another at the common surface, the first ones of the pores having an opening of a diameter that is larger than a diameter of an opening of the second one of the pores, the first one of the pores being configured and arranged to accept biological particles of a size that is larger than the diameter of the second one of the pores.

\* \* \* \* \*